(12) United States Patent
Gebhardt et al.

(10) Patent No.: US 10,816,624 B2
(45) Date of Patent: Oct. 27, 2020

(54) METHOD AND DEVICE FOR CORRECTING A B0 INHOMOGENEITY BY A RADIO FREQUENCY SIGNAL

(71) Applicant: Siemens Healthcare GmbH, Erlangen (DE)

(72) Inventors: Matthias Gebhardt, Erlangen (DE); Ralf Kartäusch, Erlangen (DE); Markus Vester, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/363,733

(22) Filed: Mar. 25, 2019

(65) Prior Publication Data

US 2019/0293740 A1     Sep. 26, 2019

(30) Foreign Application Priority Data

Mar. 26, 2018    (EP) .................... 18164022
May 9, 2018    (EP) .................... 18171548

(51) Int. Cl.
*G01R 33/46*     (2006.01)
*G01R 33/48*     (2006.01)
(Continued)

(52) U.S. Cl.
CPC ......... *G01R 33/4616* (2013.01); *A61B 5/055* (2013.01); *G01R 33/3875* (2013.01); *G01R 33/4818* (2013.01); *G01R 33/4836* (2013.01); *G01R 33/56563* (2013.01); *G01N 24/08* (2013.01); *G01R 33/34* (2013.01); *G01R 33/4831* (2013.01); *G01R 33/5659* (2013.01); *G01R 33/56572* (2013.01)

(58) Field of Classification Search
CPC .......... G01R 33/4616; G01R 33/56563; G01R 33/3875; G01R 33/4836; G01R 33/4818; G01R 33/5659; G01R 33/56572; G01R 33/4831; G01R 33/34; G01R 33/34046; G01R 33/385; G01R 33/341; G01N 24/08; A61B 5/055
See application file for complete search history.

(56) References Cited

U.S. PATENT DOCUMENTS

2014/0070805 A1*   3/2014   Van Der Meulen ........................ G01R 33/246 324/309
2015/0002149 A1*   1/2015   Nehrke ................ G01R 33/243 324/309

OTHER PUBLICATIONS

Hu Y. et al.: "Independent Band-specific Correction for B0 and B1 Inhomogeneities in Multiband 2D RF Pulses"; International Society for Magnetic Resonance in Medicine; 25th Annual Meeting & Exhibition. pp. 1-3.
(Continued)

*Primary Examiner* — G. M. A Hyder
(74) *Attorney, Agent, or Firm* — Lempia Summerfield Katz LLC (57) ABSTRACT

A method for correcting a B0 inhomogeneity in a magnetic resonance scan with a magnetic resonance tomograph is provided. The magnetic resonance tomograph includes a controller, a radio frequency unit, and a transmitting antenna. In the method, the controller determines a transmission signal that is suitable for correcting an effect of an inhomogeneity of a static B0 magnetic field in an examination volume by the Bloch-Siegert effect. The transmission signal is emitted into the examination volume.

14 Claims, 3 Drawing Sheets

(51) Int. Cl.
*G01R 33/483* (2006.01)
*A61B 5/055* (2006.01)
*G01R 33/3875* (2006.01)
*G01R 33/565* (2006.01)
G01R 33/34 (2006.01)
G01N 24/08 (2006.01)

(56) References Cited

OTHER PUBLICATIONS

Kartäusch, Ralf, et al. "Spatial phase encoding using a Bloch-Siegert shift gradient." Proceedings 21st Scientific Meeting, International Society for Magnetic Resonance in Medicine, Salt Lake City. 2013.

\* cited by examiner

METHOD AND DEVICE FOR CORRECTING A B0 INHOMOGENEITY BY A RADIO FREQUENCY SIGNAL

This application claims the benefit of EP 18164022.8, filed on Mar. 26, 2018, and EP 18171548.3, filed on May 9, 2018, which are hereby incorporated by reference in their entirety.

BACKGROUND

The present embodiments relate to B0 field correction in a magnetic resonance tomograph.

Magnetic resonance tomographs are imaging devices that, for imaging an examination object, orient nuclear spins of the examination object with a strong external magnetic field and by an alternating magnetic field, excite the nuclear spins to precession about this orientation. The precession or the return of the spin from this excited state into a state with lower energy generates an alternating magnetic field as a response, also designated a magnetic resonance signal, which is received via antennae.

With the help of magnetic gradient fields, a position encoding is impressed upon the signals, which subsequently enables an allocation of the received signal to a volume element. The received signal is then evaluated, and a three-dimensional imaging representation of the examination object is provided. The representation created gives a spatial density distribution of the spin.

The quality of the magnetic resonance tomogram is substantially dependent upon the homogeneity of the static B0 magnetic field for orienting the nuclear spin. Inhomogeneities cause both spatial distortions of the generated image, since the spatial encoding by gradient fields is also dependent upon the magnetic field strength. The image contrasts are also influenced by B0 field inhomogeneities, since the strength of the excitation also decreases on deviation of the Larmor frequency from the transmission frequency of an excitation pulse. Not least, closely adjacent Larmor frequencies may no longer be correctly separated and fat appears (e.g., as free tissue water).

B0-inhomogeneities may be caused, for example, by the field magnets themselves, materials of the magnetic resonance tomograph, or by the surroundings. These disturbances are mostly static and may be corrected, for example, by ferromagnetic materials.

For the correction of temporary field changes, shim coils are also known, through which a constant, adjustable current flows.

However, due to the different magnetic susceptibilities of tissues, inhomogeneities in the static B0 field within the patient are also caused. By reason of the position in the body and due to fundamental properties of the magnetic fields, these may be corrected only to a certain extent and not at all by external static magnetic coils. If the homogeneity of the B0 field disrupted by tissue susceptibility is to be achieved not only in a two-dimensional slice, but in a whole three-dimensional volume, the possibilities making use of external field coils operated with static currents are limited.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a device and a method for improving an image acquisition in the presence of magnetic field inhomogeneities are provided.

The method is carried out on a magnetic resonance tomograph of the present embodiments that includes a control unit, a radio frequency unit, and a transmitting antenna. In one act, a transmission signal that is suitable for correcting the effect of the inhomogeneity of the static B0 magnetic field in an examination volume is determined by the control unit using the Bloch-Siegert effect. A correction or displacement of the Larmor frequency, for example, may be a correction of the effect.

From the Bloch-Siegert effect, it is known that a Larmor frequency, given here by the static magnetic B0 field of a field magnet of the magnetic resonance tomograph at the site of the nuclear spin and the magnetic moment of the nuclear spin, may be displaced in the frequency space by an alternating magnetic field at this site with a frequency not equal to this local Larmor frequency. Thereby, the frequency shift is proportional to the square of the field strength of the alternating field and is indirectly proportional to the difference of the frequencies of the correction signal and the local Larmor frequency. Thus, from a B0 deviation at a given location, a field strength that is to be achieved may be calculated dependent upon the frequency of the correction signal with which the Larmor frequency may be displaced to, or in the direction of, the ideal Larmor frequency without a B0 inhomogeneity. In this way, a spatial field strength or power distribution that is to be achieved may also be determined over the examination region. The B0 inhomogeneity may be estimated, for example, by an empirical value (e.g., from the physiology of the patient in the examination region) and stored as a table in the magnetic resonance tomograph or may be determined by a B0 field measurement (described below) with the magnetic resonance tomograph. In one embodiment, using a multi-channel radio frequency unit, different signal components with different frequencies are generated. In one embodiment, merely for a pre-determined field distribution of a transmitting antenna (e.g., a body coil or a local coil), a frequency and an amplitude or power of the transmission signal that corrects the effect of the B0 inhomogeneity only at a selected site in the examination volume is determined. It is understood in this context as a correction if the effects of the B0 inhomogeneity on the magnetic resonance scan are substantially reduced and still represent, for example, only a deviation of less than 50%, 25% or 10% of the deviation due to the actual B0 inhomogeneity.

In a further act of the method, the transmission signal determined is generated with the radio frequency unit and emitted via the antenna into the examination volume. In one embodiment, the antenna and the radio frequency unit are the existing radio frequency transmitters for the excitation pulses and transmitting antennae such as a body coil or a local transmitting coil. However, separate transmitters and antennae may also be provided if the B0 inhomogeneity is also to be compensated for in the excitation pulse by a correcting alternating field. Thereby, the antenna alone or in combination with the radio frequency unit enables a controllable spatial field strength distribution to be achieved, as is also carried out, by way of example, with an embodiment. In conjunction with a multichannel radio frequency unit, it the frequency of the alternating magnetic field generated may also be varied spatially.

The method of one or more of the present embodiments enables a flexible correction of B0 inhomogeneities (e.g., also if the inhomogeneities are caused by susceptibility variations, the magnetization of which is not rotation-free and therefore may not be compensated for by conventional external coils at least in a three-dimensional volume).

The magnetic resonance tomograph shares the advantages of the method carried out by the magnetic resonance tomograph.

In a possible embodiment of the method, the act of determining the transmission signal further includes the act of determining a B0 inhomogeneity in the examination volume using the magnetic resonance tomograph. This may take place by acquiring or measuring a B0 map. However, based on the position and physiology, the control unit may use stored information to estimate a B0 inhomogeneity. For example, a generalized B0 map that is scaled by only of a few parameters such as position, size, weight, and circumference may be stored to estimate the B0 inhomogeneity.

The act of determining the transmission signal includes determining a frequency distribution and a spatial distribution of the transmission signal using the control unit. As already described, the displacement of the Larmor frequency by the Bloch-Siegert effect is proportional to the square of the field strength of the alternating magnetic field generated by the transmission signal and is indirectly proportional to the difference of the local Larmor frequency from the frequency of the transmission signal. The control unit establishes with this equation a transmission signal that at least partially compensates for the effect of the inhomogeneity of the B0 field. In other words, when the transmission signal is emitted via the antenna, at least at one location of the examination volume, the frequency with which the nuclear spins precess, is displaced in the direction of the Larmor frequency for the B0 value for the ideal homogeneous B0 field, so that the frequency difference is reduced, for example, by more than 50%, 80%, or 90%. In one embodiment, the correction takes place at a plurality of sites. In one embodiment, with an optimization method, the square of the deviation is minimized in that the amplitude and/or frequency of the transmission signal are varied as parameters. As described below, this amplitude and frequency may also be varied in a location-dependent manner.

The method of one or more of the present embodiments thus permits the correction of the B0 inhomogeneities to be adapted to the patient.

In an embodiment of the method, this is carried out on a magnetic resonance tomograph, the transmitting antenna of which has a plurality of antenna elements. This transmitting antenna may be, for example, a body coil with a plurality of independently controllable segments or a local transmitting coil matrix. A separate antenna with an antenna array for the transmission signal may also be provided. In the embodiment of the method, the act of transmitting includes determining a configuration of the radio frequency unit and/or the antenna elements for approximate achievement of the desired spatial distribution. In one embodiment, the radio frequency unit includes a plurality of independent channels, also designated pTX. The channels then feed different antenna elements. Using the phase position, at the same frequency, and the amplitude relationships, the spatial distribution of the transmission signal and the field strength generated thereby may be controlled at different sites. However, a controllable directional effect may also be achieved by controllable phase shift elements in the radio frequency unit or the transmitting antenna from a single radio frequency signal using a plurality of antenna elements.

In one embodiment, the frequencies of the outputs of the channels are different, so that the spatial distribution depends only on the amplitude and the selection of the controlled antenna elements with their transmitting characteristic.

For all these cases, with the laws of electrodynamics, as previously in the excitation by pTX, a configuration for the radio frequency unit and/or the transmitting antenna that generates the desired amplitude distribution and possibly frequency distribution may be determined. In a further act of the method, the radio frequency unit and/or the transmitting antenna is set according to the configuration.

Finally, in a further act, the transmission signal determined is generated with the radio frequency unit and emitted via the transmitting antenna into the examination volume. The configuration of the radio frequency unit and/or of the transmitting antenna thereby provides that the desired spatial distribution is achieved.

The plurality of the antenna elements of the transmitting antenna enable a more exact and more flexible control of the correction.

In a possible embodiment of the method, the method further includes determining a B0 map using the magnetic resonance tomograph. This may take place, for example, in that magnetic resonance signals are acquired at different echo times, and images generated therefrom are compared. Other methods for measuring are also known.

In the embodiment of the method, during determination of a B0 inhomogeneity in the examination volume using the magnetic resonance tomograph, the acquired B0 map is used in that, for example, deviations from a constant target B0 value are determined from the B0 map.

The B0 map thereby determined reproduces the actual B0 inhomogeneities in the examination volume (e.g., in the presence of the real patient). In one embodiment, the B0 map is determined using the method of one or more of the present embodiments (e.g., with a radio frequency correction signal), and so also, the effect of the correction may be detected or iteratively improved. The B0 inhomogeneities are thus determined more accurately, and the correction may take place more accurately with the method.

In an embodiment of the method, the determination of a B0 map takes place iteratively using the magnetic resonance tomograph using a correction according to the method. In one embodiment, as a starting value for the B0 inhomogeneity, a constant ideal B0 field is assumed without inhomogeneities. Then, at the start of the iteration of the measurement, initially, no transmission signal is output for the correction of the Larmor frequency. Under these conditions, according to the known method, a first (real) B0 map is measured by the magnetic resonance tomograph and is then the basis for determining a transmission signal for correcting the Larmor frequency according to the method of one or more of the present embodiments.

Using this transmission signal, a second B0 map from which inhomogeneities still not corrected by the transmission signal are determined is acquired. The second B0 map is for determining a second transmission signal according to the method of one or more of the present embodiments. This is repeated iteratively, whereby the B0 map from the iteration n−1 is always the basis for determining the n-th transmission signal.

A discontinuation may take place, for example, if the measured B0 inhomogeneities are smaller than a pre-determined discontinuation value, the inhomogeneities no longer lessen in the following act, or a maximum number of iterations is reached.

In a possible embodiment of the method, the method further includes determining a frequency distribution and power of an excitation pulse that, under the determined B0 inhomogeneity, achieves a homogeneous excitation in the examination volume. Due to the strong excitation pulses, for example, by reason of the SAR loading but also due to necessarily very high values for the amplitude of the transmission signal for correction or not least due to the use of the same radio frequency unit and/or antenna, it may be required on use of the same radio frequency unit and/or antenna, on excitation of the nuclear spin, to compensate for B0 inhomogeneities in other ways. This may take place, for example, using a broadband excitation pulse that may excite the nuclear spin with a different Larmor frequency. Given a known B0 distribution, the shape of the pulse may be determined by a discrete Fourier transform. In one act of the method, this excitation pulse is then generated by the radio frequency unit and is emitted via an excitation antenna. This may be, for example, the body coil or a local transmitting coil.

In one embodiment, the transmitting antenna of the magnetic resonance tomograph includes an array of antenna elements. In one embodiment, a phase position and/or an amplitude of the transmission signal is settable at the antenna elements. Thus, a position-dependency of the Bloch-Siegert effect may be achieved, and a B0 inhomogeneity may be better corrected.

In one embodiment of the magnetic resonance tomograph, the radio frequency unit and/or the transmitting antenna includes a protective device. The protective device is configured to protect the radio frequency unit on simultaneous emission of the transmission signal and an excitation pulse or phase encoder pulse. For example, the protective device may make the antenna or the radio frequency unit resonant to the frequency of the transmission signal so that a signal of an excitation pulse or a phase encoding pulse is damped by more than 20 dB, 40 dB, 60 dB or 100 dB at a signal output of the radio frequency unit for the transmission signal as compared with a magnetic resonance tomograph without a protective device. In one embodiment, the protective device is a blocking circuit on the transmitting antenna and/or a radio frequency unit that is resonantly matched to the frequency of the excitation pulse or the phase encoder pulse and selectively damps by more than 20 dB, 40 dB, 60 dB or 100 dB at a signal output of the radio frequency unit.

The protective device makes use thereof that for the Bloch-Siegert effect, a frequency different from a Larmor frequency of the nuclear spin to be investigated in the field B0 of the magnetic resonance tomograph is to be used, and so, the protective device may protect the radio frequency unit frequency-selectively.

Using a broadband excitation pulse, an excitation of all nuclear spins may take place without further increasing the SAR loading using an additional correction signal.

In an embodiment of the method, the act of emitting takes place during the phase encoding and/or the readout. For example, during the phase encoding, in most examination processes of a magnetic resonance tomograph, no radio frequency signals are emitted into the examination volume or received therefrom. It is thus possible to emit the transmission signal for correction without disruptive interactions. In one embodiment, this may take place with the same radio frequency unit and transmitting antenna as for the excitation pulse. During the readout (e.g., the phase of a magnetic resonance scan, during which the magnetic resonance signals are received and recorded), disruptions by the transmission signal for correction are to be prevented. This may be achieved, for example, by a suitable selection of the frequency of the transmission signal for correction using filters on the receiving side. An intermittent transmission/reception may also be provided.

In one embodiment, the transmission signal for correction is transmitted via the longest possible time of a pulse train. Thus, the amount of the correction and thus the field strength or power may be reduced.

In an embodiment of the method, in an act of the determination of the transmission signal, a temporal dependency of the frequency and/or amplitude is determined such that using the emitted transmission signal over the duration of the magnetic resonance scan, the Larmor frequency is substantially corrected as an average over time. By the Bloch-Siegert effect, it is also possible to draw the frequency with which the nuclear spin precesses beyond the Larmor frequency or to overcompensate at the ideal B0. This enables a transmission signal with temporal modulation of the frequency and/or amplitude to be determined and then also emitted such that as an average over time, a time segment without a transmission signal is corrected by a time segment with overcompensation.

In this way, for example, during a readout, the transmission may be set so as not to disrupt the reception of the MR signal, and the deviation may subsequently be corrected through overcompensation.

DETAILED DESCRIPTION

Figure 1:
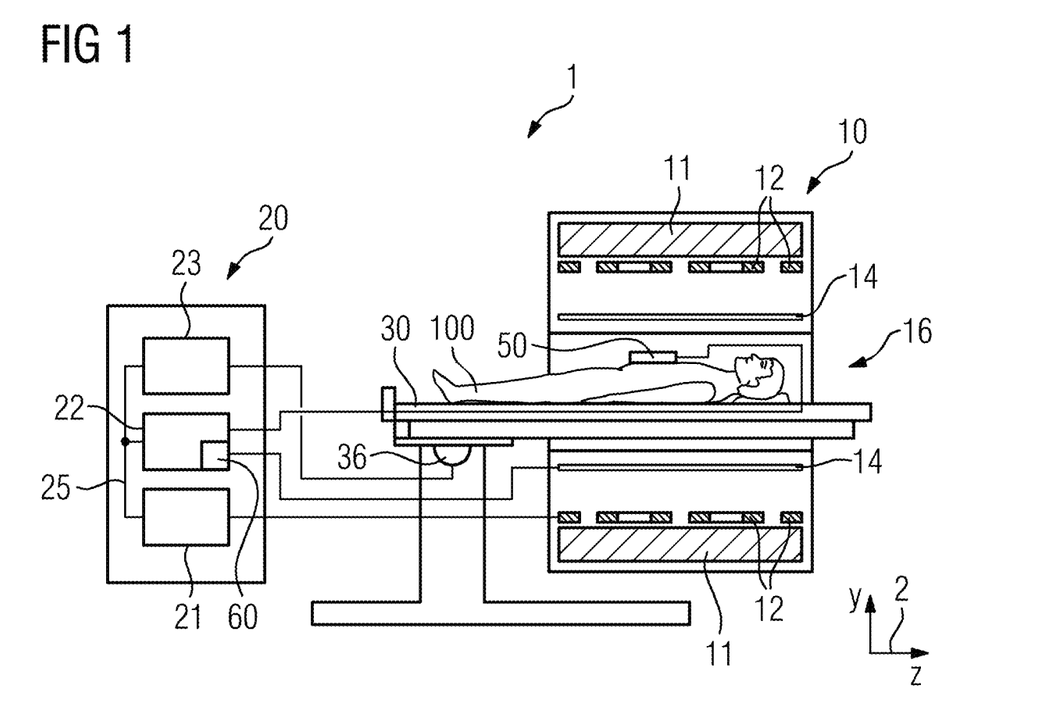
FIG. 1 shows an exemplary schematic representation of a magnetic resonance tomograph with a radio frequency unit according to an embodiment.

FIG. 1 shows a schematic representation of an embodiment of a magnetic resonance tomograph 1 (e.g., a magnet unit).

The magnet unit 10 has a field magnet 11 that generates a static magnetic field B0 for aligning nuclear spins of samples or patients 100 in a scanning region. The scanning region is arranged in a patient tunnel 16 that extends in a longitudinal direction 2 through the magnet unit 10. A patient 100 is movable by a patient table 30 and a positioning unit 36 of the patient table 30 into the scanning region. Typically, the field magnet 11 is a superconducting magnet that may provide magnetic fields with a magnetic flux density of up to 3T or even higher (e.g., in the newest devices). For weaker field strengths, however, permanent magnets or electromagnets with normally conducting coils may also be used.

The magnet unit 10 further includes gradient coils 12 that are configured, for spatial differentiation of captured imaging regions in an examination volume, to overlay variable magnetic fields onto the magnetic field B0 in three spatial directions. The gradient coils 12 are typically coils made of normally conducting wires that may generate mutually orthogonal fields in the examination volume.

The magnet unit 10 also has a body coil 14 that is configured to emit a radio frequency signal fed via a signal line 33 into the examination volume, to receive resonance signals emitted from the patient 100, and to pass the received resonance signals on via a signal line. In one embodiment, the body coil 14 is replaced, for the emission of the radio frequency signals and/or the reception, by local coils 50 that are arranged in the patient tunnel 16 close to the patient 100. In one embodiment, the local coil 50 is configured for transmitting and receiving, and therefore, a body coil 14 may be omitted.

A control unit 20 (e.g., a controller) supplies the magnet unit 10 with the different signals for the gradient coils 12 and the body coil 14 and evaluates the received signals. A magnetic resonance tomograph control system 23 thereby coordinates the subsidiary units.

Thus, the control unit 20 includes a gradient controller 21 that is configured to supply the gradient coils 12 via feed lines with variable currents that provide the desired gradient fields in the examination volume in a temporally coordinated manner.

The control unit 20 also includes a radio frequency unit 22 that is configured to generate a radio frequency pulse with a pre-determined temporal sequence, amplitude, and spectral power distribution for excitation of a magnetic resonance of the nuclear spin in the patient 100. Thereby, pulse power levels in the region of kilowatts may be achieved. The individual units are connected to one another via a signal bus 25.

The radio frequency signal generated by the radio frequency unit 22 is fed via a signal connection to the body coil 14 and is emitted into the body of the patient 100 in order to excite the nuclear spin at the body of the patient 100. An emission of the radio frequency signal via one or more coil windings of the local coil matrix 50 may also be provided.

In one embodiment, according to a method, the radio frequency unit 22 and the body coil 14 and/or the local coil 50 may be used for correcting the Larmor frequency.

The local coil matrix 50 may receive a magnetic resonance signal from the body of the patient 100 since, due to the small distance, the signal-to-noise ratio (SNR) of the local coil 50 is better than with a reception by the body coil 14. The MR signal received by the local coil matrix 50 is preprocessed in the local coil 50 and passed on to the radio frequency unit 22 of the magnetic resonance tomograph 1 for evaluation and image acquisition. In one embodiment, the signal connection 33 is used for this, although a wireless transfer may, for example, also be provided.

Figure 2:
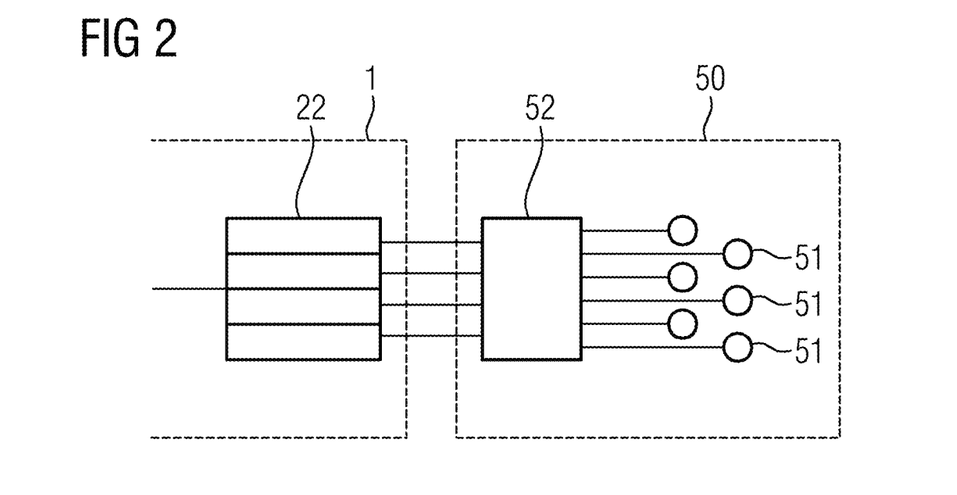
FIG. 2 shows an exemplary schematic representation of a radio frequency unit and a local coil for carrying out an embodiment of a method.

FIG. 2 shows an exemplary embodiment of a radio frequency unit 22 and a local coil matrix 50 for carrying out the method. The radio frequency unit 22 has a plurality of oscillators and amplifiers for generating a plurality of radio frequency signals. Using the separate oscillators, signals of different frequency and phase may be generated independently of one another. The separate amplifier also permits the amplitude to be set independently. In the following, an oscillator together with the amplifier in signal connection therewith is denoted as the transmitting channel. The radio frequency unit 22 with the transmitting channels may also be used for exciting the nuclear spin (e.g., in a pTX magnetic resonance tomograph).

The radio frequency signals generated by the radio frequency unit 22 are passed on to a switching matrix 52. The switching matrix 52 is configured to create a signal connection between the radio frequency unit 22 and a coil winding 51 of the local coil matrix 50, so that the radio frequency signal is converted into a magnetic radio frequency alternating field. In principle, however, the antenna coils may be directly connected to the radio frequency unit 22; there then exists, however, a fixed allocation, and the maximum number of usable antenna coils is equal to the number of channels.

The switching matrix 52 may thereby possess switching elements that pass on signals, as far as possible without change, from the radio frequency unit 22 to a selectable antenna coil or coil winding 51. In this way, the spatial distribution of the emitted field may be changed, and with the existing channels, a region may be selected from a plurality of coils without, for example, the local matrix having to be spatially displaced.

In one embodiment, the switching matrix 52 has settable or connectable phase-shifters and/or adder members and/or attenuators that allow the input signals from the radio frequency unit 22 to be combined to different new signals with changeable phase and amplitude, where the number of signals generated and thus also the number of the antenna coils suppliable with a signal may be greater than the number of channels. In principle, with such a switching matrix, a local coil matrix 50 having a plurality of antenna coils 51 may be supplied with signals from a radio frequency unit with one channel provided the signals have the same frequency. Such a switching matrix 52 advantageously increases the flexibility and the usage possibilities of the method of one or more of the present embodiments without driving up the costs as a result of many channels in the radio frequency unit.

The switching matrix 52 may thereby also be part of the radio frequency unit 22, although the advantage of the low number of distribution lines between the radio frequency unit 22 and the local coil matrix 50 then becomes lost.

Using the radio frequency unit 22, the local coil matrix 50 or the body coil 14, and possibly the switching matrix 52, a plurality of spatial distributions of an alternating magnetic field of one frequency or a plurality of fields of differing frequency may be generated for the method described below.

Figure 3:
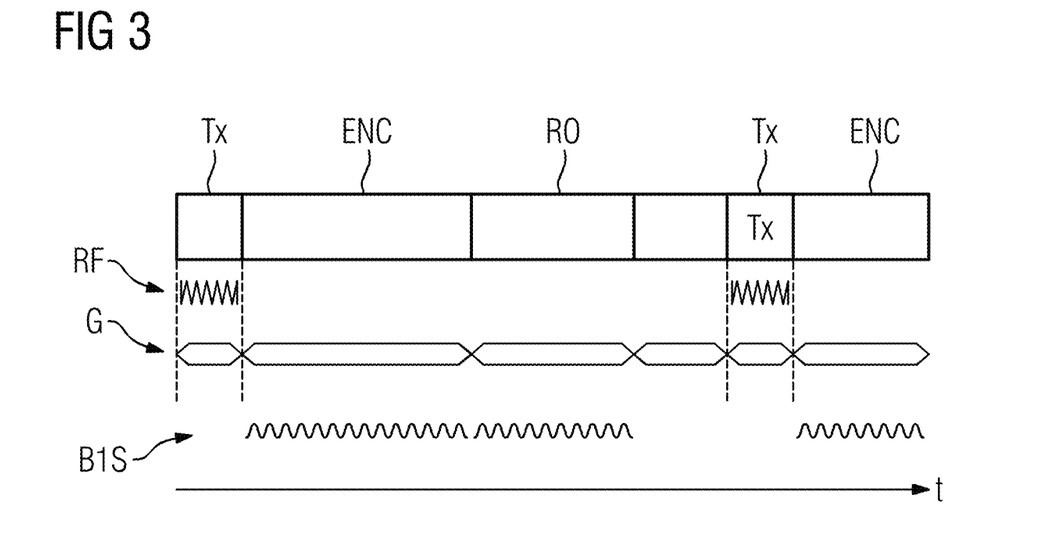
FIG. 3 shows an exemplary chronological sequence of a magnetic resonance scan with the method.

FIG. 3 shows an exemplary chronological sequence of a magnetic resonance scan for an image acquisition. The time axis runs to the right. In the upper bar, the individual phases of a magnetic resonance scan are shown. A scan cycle, also designated a pulse train, begins with an excitation of nuclear spins by an excitation pulse, denoted TX here. Thereupon, there follows a phase encoding ENC for impressing a spatial orientation onto the nuclear spin. In the phase denoted as readout RO, the magnetic resonance signals are received and recorded or evaluated. Thereafter, a pause may follow in which, for example, the nuclear spins relax before a new excitation takes place.

In FIG. 3 from top to bottom, the lines for different signals are shown. RF denotes the radio frequency signal with which the excitation takes place. G denotes the gradient signals of the gradient coils. Finally, B1S denotes the radio frequency signal of one or more of the present embodiments for correction of a B0 inhomogeneity.

Figure 4:
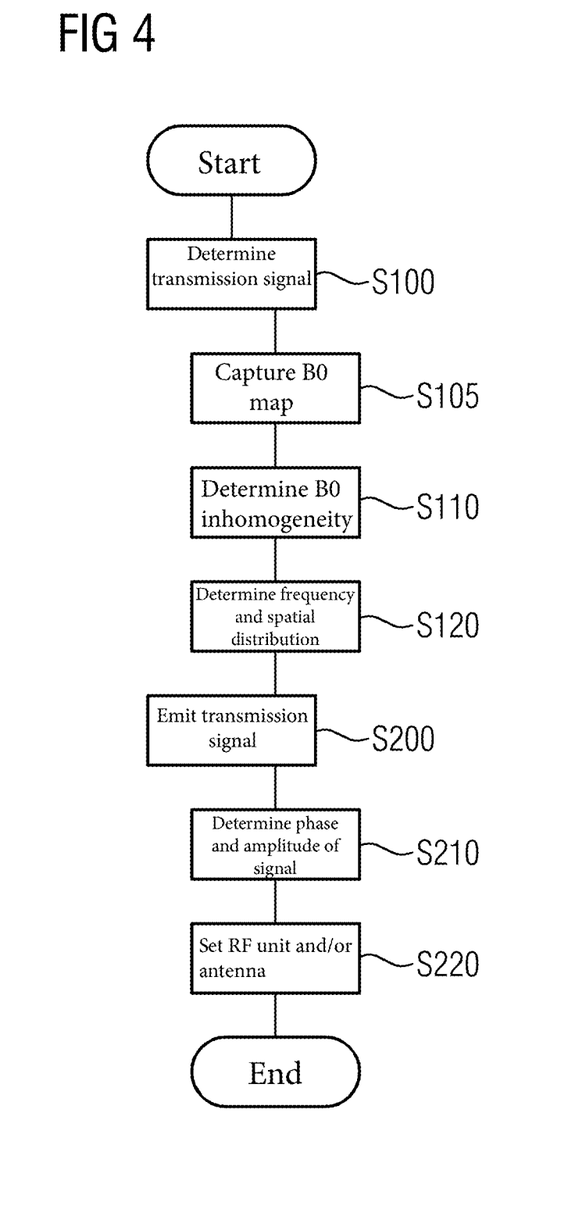
FIG. 4 shows a schematic flow diagram of a method according to an embodiment.

In FIG. 4, an exemplary schematic flow chart of an embodiment of the method is shown.

The method of FIG. 4 for correction of a B0 inhomogeneity is divided into the two main acts S100 and S200. In act S100, initially a transmission signal that is suitable for correcting the effect of the inhomogeneity in an examination volume using the Bloch-Siegert effect is determined by the control unit 20.

For this purpose, the B0 inhomogeneity is first to be known. It is thereby conceivable that in subact S105, by scanning, a B0 map is captured by the magnetic resonance tomograph 1. For this purpose, for example, two magnetic resonance tomograms may be generated. Magnetic resonance signals of the two magnetic resonance tomograms have been measured at different echo times. From the B0 map, the control system may determine the B0 inhomogeneity in act S110.

In one embodiment, the B0 inhomogeneity is estimated using stored values from the position and other parameters of the patient. The stored values may thereby be based on a physiological model or scan values that are scaled for the patient.

In a subact S120, the control unit determines a frequency distribution and a spatial distribution of the transmission signal with which, according to the Bloch-Siegert effect, the effect of the B0 inhomogeneity is at least partially compensated for by the transmission signal in an examination volume. It is thereby also conceivable that the frequency distribution is such that the frequency of the transmission signal is constant overall.

In this case, the spatial amplitude distribution is proportional to the square of the B0 inhomogeneity, and the target distribution may be determined directly. If the frequency is also variable, then, for example, a numerical optimization method that uses the deviation of the Larmor frequency squared as an error and minimizes this by varying the frequency and the field strength may be used. Boundary conditions thereby are the properties of the radio waves and coil windings 51 for transmitting, as described in relation to S210.

In the simplest case, a correction may be required only at a single point, and for this, a single frequency and a field strength (e.g., a homogeneous field strength) are determined.

Subsequently, in the main act S200, by transmission, the determined frequency and spatial distribution are to be implemented. Thereby, for example, the calculation method used in the SAR determination may be applied.

According to Maxwell's laws and the geometry of the antennae, in subact S210, the control unit determines the signals to be fed to the antennae in phase and amplitude. For different frequencies, provided they are used, this may take place separately. Optimization methods that minimize the deviation between the distribution to be expected due to the electrodynamics and the previously determined target distribution may again be used. Therefrom, the control unit 20 determines the settings or configuration of the radio frequency unit 22 and/or the antenna elements that subsequently generate and radiate the determined signals with corresponding phase and amplitude.

In a subact S220, the control unit 22 carries out the setting of the radio frequency unit 22 and/or antenna or the switching matrix. In a subact S230, the control unit 22 triggers the generation of the determined transmission signal in the radio frequency unit 22, so that the generated determined transmission signal is emitted according to the determined configuration by the antenna elements into the examination volume and there corrects the Larmor frequency as intended.

As shown in FIG. 4, there are phases in a magnetic resonance scan that are free from other radio frequency signals required for magnetic resonance tomogram. For example, the phase during the encoding by the gradients is especially suitable for using the method of one or more of the present embodiments. At this time point, a common radio frequency unit 22 and antenna may be used for the excitation pulse and the transmission signal for correction, since the two phases take place one after the other.

During the excitation pulse, the possibility also exists of correcting the inhomogeneity solely through a frequency broadening of the pulse.

During the readout (e.g., the scanning of the magnetic resonance signals), no signals may disturb the reception at the Larmor frequency. Here, a correction according to the method may be provided in that the receiver has corresponding input filters that, for correction, block out or suppress the transmission signal of one or more of the present embodiments that has a frequency beside the ideal Larmor frequency.

In one embodiment, an intermittent reception and, therebetween, transmission of the transmission signal for correction are provided. Thereby, using a higher amplitude and/or a greater frequency deviation of the transmission signal, the deviation of the Larmor frequency in the transmission pauses is compensated for so that, averaged over time, a correct or ideal Larmor frequency is achieved.

Although the invention has been illustrated and described in detail with the exemplary embodiments, the invention is not restricted by the examples given, and other variations may be derived therefrom by a person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for correcting a B0 inhomogeneity in a magnetic resonance scan with a magnetic resonance tomograph, wherein the magnetic resonance tomograph comprises a controller, a radio frequency unit, and a transmitting antenna, wherein the method comprises:
   determining, by the controller, a transmission signal for correcting an effect of a magnetic field inhomogeneity in an examination volume by the Bloch-Siegert effect, wherein determining the transmission signal comprises:
      determining, by the magnetic resonance tomograph, a B0 inhomogeneity in the examination volume; and
      determining, by the controller, a frequency distribution and a spatial distribution of the transmission signal, with which according to the Bloch-Siegert effect, an effect of the B0 inhomogeneity is at least partially compensated for a three-dimensional imaging representation of the examination object in the examination volume by providing a spatial density distribution of a nuclear spin of the examination object; and
   emitting the transmission signal into the examination volume.

2. The method of claim 1, wherein the transmitting antenna comprises a plurality of antenna elements,
   wherein emitting the transmission signal in the examination volume comprises:

determining a configuration of the radio frequency unit, the plurality of antenna elements, or the radio frequency unit and the plurality of antenna elements for approximate achievement of a desired spatial distribution;

setting the radio frequency unit, the transmitting antenna, or the radio frequency unit and the transmitting antenna according to the determined configuration; and generating the determined transmission signal with the radio frequency unit and transmitting the generated determined transmission signal by the transmitting antenna.

3. The method as of claim 1, further comprising determining a B0 map using the magnetic resonance tomograph, wherein determining the B0 inhomogeneity comprises determining the B0 inhomogeneity in the examination volume based on the determined B0 map.

4. The method of claim 3, wherein determining the B0 map comprises determining the B0 map iteratively using a method for correction, the method for correction comprising the determining of the transmission signal and the emitting of the transmission signal into the examination volume.

5. The method of claim 1, further comprising:
determining an excitation pulse having a frequency distribution and a power that, under the determined B0 inhomogeneity, achieves a homogeneous excitation in the examination volume; and
emitting the determined excitation pulse using the transmitting antenna.

6. The method of claim 1, wherein the emitting comprises emitting during phase encoding, readout, or phase encoding and readout.

7. The method of claim 1, wherein determining the transmission signal comprises determining a temporal dependency of a frequency, an amplitude, or the frequency and the amplitude such that by the emitted transmission signal over a duration of the magnetic resonance scan, the Larmor frequency is substantially corrected as an average over time.

8. A magnetic resonance tomograph comprising:
a controller configured to determine a transmission signal for correcting an effect of a magnetic field inhomogeneity in an examination volume by the Bloch-Siegert effect, wherein determining the transmission signal comprises determining, by the controller, a frequency distribution and a spatial distribution of the transmission signal, with which according to the Bloch-Siegert effect, an effect of a B0 inhomogeneity is at least partially compensated for a three-dimensional imaging representation of an examination object in the examination volume by providing a spatial density distribution of a nuclear spin of the examination object;
a radio frequency unit; and
a transmitting antenna configured to emit the transmission signal into the examination volume, wherein the transmitting antenna comprises an array of antenna elements, wherein the spatial distribution of the transmission signal is based on the array of antenna elements.

9. The magnetic resonance tomograph of claim 8, wherein the radio frequency unit, the transmitting antenna, or the radio frequency unit and the transmitting antenna comprise a protective device that is configured to protect the radio frequency unit on simultaneous emission of the transmission signal and an excitation pulse or a phase encoder pulse.

10. In a non-transitory computer-readable storage medium that stores instructions executable by a controller of a magnetic resonance tomograph to correct a B0 inhomogeneity in a magnetic resonance scan with the magnetic resonance tomograph, wherein the magnetic resonance tomograph further comprises a radio frequency unit and a transmitting antenna, wherein the instructions comprise:
determining, by the controller, a transmission signal for correcting an effect of a magnetic field inhomogeneity in an examination volume by the Bloch-Siegert effect, wherein the determining of the transmission signal comprises:
determining, by the magnetic resonance tomograph, a B0 inhomogeneity in the examination volume; and
determining, by the controller, a frequency distribution and a spatial distribution of the transmission signal, with which according to the Bloch-Siegert effect, an effect of the B0 inhomogeneity is at least partially compensated for in the examination volume by the transmission signal;
emitting the transmission signal into the examination volume; and
determining a B0 map using the magnetic resonance tomograph, wherein determining the B0 map comprises determining the B0 map iteratively using a method for correction, the method for correction comprising the determining of the transmission signal and the emitting of the transmission signal into the examination volume, wherein determining the B0 inhomogeneity comprises determining the B0 inhomogeneity in the examination volume based on the determined B0 map.

11. The non-transitory computer-readable storage medium of claim 10, wherein the transmitting antenna comprises a plurality of antenna elements,
wherein emitting the transmission signal in the examination volume comprises:
determining a configuration of the radio frequency unit, the plurality of antenna elements, or the radio frequency unit and the plurality of antenna elements for approximate achievement of a desired spatial distribution;
setting the radio frequency unit, the transmitting antenna, or the radio frequency unit and the transmitting antenna according to the determined configuration; and
generating the determined transmission signal with the radio frequency unit and transmitting the generated determined transmission signal by the transmitting antenna.

12. The non-transitory computer-readable storage medium of claim 10, wherein the instructions further comprise:
determining an excitation pulse having a frequency distribution and a power that, under the determined B0 inhomogeneity, achieves a homogeneous excitation in the examination volume; and
emitting the determined excitation pulse using the transmitting antenna.

13. The non-transitory computer-readable storage medium of claim 10, wherein the emitting comprises emitting during phase encoding, readout, or phase encoding and readout.

14. The non-transitory computer-readable storage medium of claim 10, wherein determining the transmission signal comprises determining a temporal dependency of a frequency, an amplitude, or the frequency and the amplitude such that by the emitted transmission signal over a duration of the magnetic resonance scan, the Larmor frequency is substantially corrected as an average over time.

\* \* \* \* \*